(12) United States Patent
Buss

(10) Patent No.: US 9,227,021 B2
(45) Date of Patent: Jan. 5, 2016

(54) MICRONEEDLE ROLLER (MNR) INFUSION SYSTEM

(75) Inventor: Brian Buss, Plano, TX (US)

(73) Assignee: GENESIS BIOSYSTEMS, INC., Lewisville, TX (US)

(*) Notice: Subject to any disclaimer, the term of this patent is extended or adjusted under 35 U.S.C. 154(b) by 1097 days.

(21) Appl. No.: 13/172,322

(22) Filed: Jun. 29, 2011

(65) Prior Publication Data
US 2011/0319865 A1    Dec. 29, 2011

Related U.S. Application Data

(60) Provisional application No. 61/359,697, filed on Jun. 29, 2010.

(51) Int. Cl.
| A61M 5/42 | (2006.01) |
| A61M 5/31 | (2006.01) |
| A61M 5/32 | (2006.01) |
| A61M 5/46 | (2006.01) |
| A61M 37/00 | (2006.01) |
| A61M 5/158 | (2006.01) |

(52) U.S. Cl.
CPC .............. *A61M 5/425* (2013.01); *A61M 5/3134* (2013.01); *A61M 5/3287* (2013.01); *A61M 5/3293* (2013.01); *A61M 5/46* (2013.01); *A61M 37/0015* (2013.01); *A61M 2005/1585* (2013.01); *A61M 2037/0023* (2013.01); *A61M 2037/0061* (2013.01)

(58) Field of Classification Search
CPC ................ A61M 37/0015; A61M 2037/0023; A61M 2005/1452; A61M 2037/0007; A61M 5/14248; A61M 5/155; A61M 5/425; A61M 2037/003; A61M 2037/0046; A61M 2005/14284; A61M 2005/1585; A61M 2205/353; A61M 35/00; A61M 39/0208; A61M 5/158; A61M 2037/0053; A61M 2005/14252; A61M 2005/31598; A61M 5/002; A61M 5/14216; A61M 5/1422; A61M 5/16809; A61M 5/3129; A61B 5/14514; A61B 5/150099; A61B 5/150389; A61B 5/150412; A61B 5/150145; A61B 5/15016; A61B 5/150442; A61B 5/150984; B65D 81/20
USPC .......................... 604/506, 173, 140, 272, 176
See application file for complete search history.

(56) References Cited

U.S. PATENT DOCUMENTS

| 5,865,796 A * | 2/1999 | McCabe .......................... 604/71 |
| 6,743,211 B1 * | 6/2004 | Prausnitz et al. .............. 604/239 |
| 7,410,476 B2 | 8/2008 | Wilkinson et al. |

(Continued)

FOREIGN PATENT DOCUMENTS

WO    2004082469 A2    9/2004

*Primary Examiner* — Kami A Bosworth
*Assistant Examiner* — Brandy S Lee
(74) *Attorney, Agent, or Firm* — Edwin S. Flores; Daniel J. Chalker; Chalker Flores, LLP

(57) ABSTRACT

A micro-needle roller (MNR) infusion system for transdermal delivery of active agents, skin-care products, and other topical formulations is described herein. The infusion system of the instant invention comprises a needle roller assembly with 0.25 mm needles enclosed in a housing with a vacuum line and a disposable cartridge having the active agent, the skin-care product or the topical formulation. The vacuum delivers the fluid and ensures that the skin is being pulled against the needle wheel surface to ensure that penetration of the needles is complete into the skin, simultaneously the fluid is flowing to the wheel and to skin as it rolls along with the outer housing of the tip cap assembly being occluded to the skin surface.

34 Claims, 4 Drawing Sheets

(56) References Cited

U.S. PATENT DOCUMENTS

| | | |
|---|---|---|
| 7,658,728 B2 | 2/2010 | Yuzhakov |
| 2006/0051404 A1* | 3/2006 | Yeshurun et al. ............ 424/449 |
| 2007/0161964 A1* | 7/2007 | Yuzhakov .................... 604/272 |
| 2008/0140049 A1 | 6/2008 | Kirby |
| 2010/0042050 A1 | 2/2010 | Chowdhury |
| 2010/0256594 A1* | 10/2010 | Kimmell et al. ............. 604/506 |

* cited by examiner

MICRONEEDLE ROLLER (MNR) INFUSION SYSTEM

CROSS-REFERENCE TO RELATED APPLICATIONS

This application claims priority to U.S. Provisional Application Ser. No. 61/359,697 filed Jun. 29, 2010, the content of which is incorporated by reference herein in its entirety.

TECHNICAL FIELD OF THE INVENTION

The present invention relates in general to the field of transdermal delivery system, and more particularly, to a microneedling system that enhances transdermal delivery of active agents skin-care products and other topical formulations.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with the microneedle arrays, methods for transdermal drug delivery and in general to devices for the administration of active agents to patients through the skin.

U.S. Pat. No. 7,658,728 (Yuzhakov, 2010) discloses microneedle arrays and drug delivery devices for transdermally delivering a drug formulation to a patient. The microneedle array device includes a substantially planar substrate having an array of apertures; and a plurality of microneedles projecting at angle from the planar substrate, the microneedles having a base portion integrally connected to the substrate, a tip end portion distal to the base portion, and body portion therebetween, wherein each microneedle has at least one channel extending substantially from the base portion through at least a part of the body portion, the channel being open along at least part of the body portion and in fluid communication with at least one of the apertures in the substrate.

U.S. Patent Application No. 20080140049 (Kirby, 2008) describes a device for transport of material across or into a biological barrier, the device includes a puncturing projection associated with a first portion of a substrate, the first portion of the substrate being movable between a first substrate position in which, in use, the puncturing projection is in puncturing contact with the biological barrier so as to form a flow path for said material across or into said biological barrier and a second substrate position in which, in use, the puncturing projection is at least partially retracted from the first position, wherein the substrate is resiliently deformable or displaceable from the first to the second substrate position by a biasing device associated with the substrate.

U.S. Patent Application No. 20100042050 (Chowdhury, 2010) discloses a drug delivery device that delivers pharmacologically active substances transdermally using microneedles arranged on a belt mounted rotatably about a plurality of rollers, the microneedles having an associated drug reservoir mounted on the belt which is compressed when the needles and belt are brought into contact with the skin.

Patent Application WO/2004/082469 (Karasiuk, 2004) relates to a device, a system employing the device and method of performing skin treatment are provided for skin treatment. The device of the Karasiuk invention includes a vacuum head base defining a chamber therein and having a substantially smooth treatment tip attached and extending from an end thereof or integral therewith. The tip has at least one central opening that is open to the chamber, and is adapted to contact the skin and traverse the skin in a substantially non-abrasive manner. A vacuum access opening is provided through a side wall of the vacuum head base and adapted to connect with a source of vacuum. A tissue stop member is located within the chamber. It may have an abrasive surface for exfoliating skin cells, or a smoother surface for traversing the skin without substantial abrasion.

SUMMARY OF THE INVENTION

The present invention describes a micro-needle roller (MNR) system for delivering active agents, skin-care products or other topical formulations by mechanically perforating the outer skin layer in the presence of one or more active agents in a controlled environment that allows for transdermal absorption of the active compounds in a stable delivery environment that maximized the delivery of the one or more active agents.

The instant invention in one embodiment discloses a device for a transdermal delivery of one or more active agents to a subject comprising: a housing comprising a cavity, wherein the cavity is adapted to receive one or more gas lines, vacuum lines or both, one or more reservoirs, cartridges or both, and one or more active agents contained in the cavity or in the removable reservoirs or cartridges and a tip cap assembly removably attached to the housing assembly, wherein the tip cap assembly encloses a skin penetrating device in fluid connection with the cavity in the housing, wherein the skin penetrating device comprises a micro-needle roller comprising one or more micro-needles attached to and supported by a roller surface, wherein a movement of the roller over the skin of the subject causes a rotation of the roller and brings the micro-needles into contact with the skin of the subject through an opening in the tip cap assembly resulting in a penetration of the skin and the transdermal delivery of the active agent, the skin-care product, the topical formulation or combinations thereof present on the roller.

In one aspect of the device of the instant invention the housing assembly further comprises a switch, a button or combinations or modifications thereof for powering the device, turning on a vacuum, or moving the roller assembly. In another aspect a flow of the active agent to the roller surface is controlled by vacuum. In another aspect a pulling of the skin of the subject to the roller surface for penetration is controlled by vacuum. In yet another aspect the micro-needles have lengths of 0.2 mm, 0.25 mm, 0.5 mm, 1.0 mm, and 1.5 mm. In a specific aspect the micro-needle length is 0.25 mm.

In one aspect the housing comprises a material selected from the group consisting of a polymer, a metal, a mineral, a ceramic, and a glass. In another aspect the active agent comprises a formulation selected from the group consisting of a solution, a suspension, an emulsion, a lotion, a hydrogel, a semi-solid formulation, a cream, and an emollient. In another aspect the active agent comprises a therapeutic or a prophylactic drug, wherein the drug is selected from the group consisting of analgesic agent, an anti-inflammatory agent, an antiallergic agent, a steroid, a local anesthetic, a muscle relaxant, an anti-itch agent, an anti-bacterial agent, an anti-fungal agent, and combinations and modifications thereof.

In another embodiment the present invention provides for a method for transdermal delivery of one or more one or more active agents, skin-care products, topical formulations or combinations thereof to a subject comprising the steps of: (i) identifying a subject in need of the transdermal delivery, (ii) providing a transdermal delivery device comprising: a housing assembly comprising a cavity, wherein the cavity encloses a vacuum line, a vacuum chamber or any vacuum generating device, and one or more removable reservoirs, cartridges or compartments, wherein the active agent, the skin-care product or the topical formulation is contained in the one or more reservoirs or compartments and a tip cap assembly removably attached to the housing assembly, wherein the tip cap assembly encloses a skin penetrating device in fluid connection with the cavity in the housing, wherein the skin penetrating device comprises a micro-needle roller comprising one or more micro-needles attached to and supported by a roller surface, (iii) depressing a switch or a button on the housing assembly to powering on the device and turn on a vacuum, (iv) moving the roller over the skin of the subject repeatedly thereby causing a rotation of the roller, and (v) contacting the micro-needles with the skin of the subject through an opening in the tip cap assembly resulting in a penetration of the skin and the transdermal delivery of the active agent, the skin-care product, the topical formulation or combinations thereof present on the roller through an opening in the tip cap assembly.

In one aspect of the delivery method described hereinabove the flow of the active agent, the skin-care product or the topical formulation to the roller surface is controlled by vacuum. In another aspect a pulling of the skin of the subject to the roller surface for penetration is controlled by vacuum. In another aspect a micro-needle length is 0.25 mm. In yet another aspect the housing comprises a material selected from the group consisting of a polymer, a metal, a mineral, a ceramic, and a glass. In one aspect the active agent, the skin-care product or the topical formulation is selected from the group consisting of a solution, a suspension, an emulsion, a lotion, a hydrogel, a semi-solid formulation, a cream, and an emollient. In another aspect the active agent comprises a therapeutic or a prophylactic drug, wherein the drug is selected from the group consisting of analgesic agent, an anti-inflammatory agent, an antiallergic agent, a steroid, a local anesthetic, a muscle relaxant, an anti-itch agent, an anti-bacterial agent, an anti-fungal agent, and combinations and modifications thereof. In yet another aspect the skin-care products are selected from the group consisting of cleansers, toners, exfoliants, moisturizers, boosters, skin rejuvenating agents, anti-wrinkle agents, dry vacuum needling, and combinations or modifications thereof.

Yet another embodiment of the instant invention discloses a method of treating a skin condition in a subject by a delivery of one or more one or more active agents, skin-care products, topical formulations or combinations thereof to a subject comprising the steps of: (i) identifying a subject in need of treatment against the skin condition, (ii) providing a transdermal delivery device comprising: a housing assembly comprising a cavity, wherein the cavity encloses a vacuum line, a vacuum chamber or any vacuum generating device, and one or more of removable reservoirs, cartridges or compartments, wherein the active agent, the skin-care product or the topical formulation is contained in the one or more reservoirs or compartments and a tip cap assembly removably attached to the housing assembly, wherein the tip cap assembly encloses a skin penetrating device in fluid connection with the cavity in the housing, wherein the skin penetrating device comprises a micro-needle roller comprising one or more micro-needles attached to and supported by a roller surface, (iii) depressing a switch or a button on the housing assembly to powering on the device and turn on a vacuum, (iv) moving the roller over the skin of the subject repeatedly thereby causing a rotation of the roller, and (v) contacting the micro-needles with the skin of the subject through an opening in the tip cap assembly resulting in a penetration of the skin and the transdermal delivery of the active agent, the skin-care product, the topical formulation or combinations thereof present on the roller through an opening in the tip cap assembly. In one aspect the skin conditions are selected from the group consisting of bacterial, viral and fungal skin infections, skin rashes, itching, redness, swelling, burning, itching, allergies, dermatitis, hives, acne, psoriasis, eczema, wrinkles, dryness, rosacea, shingles, sunburn, skin cancers, flakes, scars, striae, and combinations and modifications thereof. In another aspect a flow of the active agent, the skin-care product or the topical formulation to the roller surface is controlled by vacuum. In another aspect a pulling of the skin of the subject to the roller surface for penetration is controlled by vacuum. In a specific aspect the micro-needle length is 0.25 mm.

In yet another aspect the active agent comprises a therapeutic or a prophylactic drug, wherein the drug is selected from the group consisting of analgesic agent, an anti-inflammatory agent, an antiallergic agent, a steroid, a local anesthetic, a muscle relaxant, an anti-itch agent, an anti-bacterial agent, an anti-fungal agent, and combinations and modifications thereof. In another aspect the skin-care products are selected from the group consisting of cleansers, toners, exfoliants, moisturizers, boosters, skin rejuvenating agents, anti-wrinkle agents, dry vacuum needling, and combinations or modifications thereof.

The present invention further discloses a device for a transdermal delivery of one or more active agents, skin-care products, topical formulations or combinations thereof to a subject comprising: a housing assembly comprising a cavity, wherein the cavity encloses a vacuum line, a vacuum chamber or any vacuum generating device, and one or more of removable reservoirs, cartridges or compartments, wherein the active agent, the skin-care product or the topical formulation is contained in the one or more reservoirs or compartments and a tip cap assembly removably attached to the housing assembly, wherein the tip cap assembly encloses a skin penetrating device in fluid connection with the cavity in the housing, wherein the skin penetrating device comprises a micro-needle roller, wherein one or more micro-needles attached to and supported by a roller surface and one or more micro-channels along the micro-needles, wherein a movement of the roller over the skin of the subject causes a rotation of the roller and brings the micro-needles into contact with the skin through an opening in the tip cap assembly resulting in a penetration of the skin and the transdermal delivery of the active agent, the skin-care product, the topical formulation or combinations thereof through the through the micro-channels along the micro-needles. In one aspect of the device described herein, the flow of the active agent, the skin-care product or the topical formulation to the micro-channels is controlled by vacuum. In another aspect the pulling of the skin of the subject to the roller surface for penetration is controlled by vacuum.

One embodiment of the present invention relates to a device for a transdermal delivery of one or more active agents, skin-care products, topical formulations or combinations thereof to a subject comprising: a housing assembly comprising a cavity, wherein the cavity encloses a vacuum line, a vacuum chamber or any vacuum generating device, and one or more of removable reservoirs, cartridges or compartments, wherein the active agent, the skin-care product or the topical formulation is contained in the one or more reservoirs or compartments and a tip cap assembly removably attached to the housing assembly, wherein the tip cap assembly encloses a skin penetrating device in fluid connection with the cavity in the housing, wherein the skin penetrating device comprises a micro-needle roller, wherein one or more hollow micro-needles are attached to and supported by a roller surface, wherein a movement of the roller over the skin of the subject causes a rotation of the roller and brings the micro-needles into contact with the skin through an opening in the tip cap assembly resulting in a penetration of the skin and the trans-dermal delivery of the active agent, the skin-care product, the topical formulation or combinations thereof through the through the hollow micro-needles. In one aspect of the device of the present invention the flow of the active agent, the skin-care product or the topical formulation to the hollow micro-needles is controlled by vacuum. In another aspect the pulling of the skin of the subject to the roller surface for penetration is controlled by vacuum.

In yet another embodiment the instant invention provides a device for a transdermal delivery of one or more active agents, skin-care products, topical formulations or combinations thereof to a subject comprising: a housing assembly comprising a cavity, wherein the cavity encloses a vacuum line, a vacuum chamber or any vacuum generating device, and one or more of removable reservoirs, cartridges or compartments and a tip cap assembly removably attached to the housing assembly, wherein the tip cap assembly encloses a skin penetrating device in fluid connection with the cavity in the housing, wherein the skin penetrating device comprises a barrel with one or more micro-needles attached to a barrel surface, wherein the barrel is a reservoir filled with the one or more one or more active agents, skin-care products or topical formulations or encloses a cartridge filled with the one or more one or more active agents, skin-care products or topical formulations wherein a movement of the barrel over the skin of the subject causes a rotation of the barrel and brings the micro-needles into contact with the skin through an opening in the tip cap assembly resulting in a penetration of the skin and the transdermal delivery of the active agent, the skin-care product, the topical formulation or combinations thereof. In one aspect the flow of the active agent, the skin-care product or the topical formulation from the barrel is controlled by vacuum, pressure or a combination of both. In another aspect the pulling of the skin of the subject to the barrel surface for penetration is controlled by vacuum.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The instant invention describes a micro-needle roller (MNR) infusion system for enhancing transdermal delivery of active ingredients and skin-care products. The MNR infusion system treatment has no side effects, does not cause any permanent damage is easy-to-use, is cost effective, and has a wide variety of applications.

Medical needling can be an alternative to laser resurfacing in patients not suitable for laser treatment or wishing to have a less invasive procedure with fewer risks. Conventional treatments frequently involve expensive, highly invasive procedures, chemical peels or laser re-surfacing. These procedures have at times offered inconsistent or disappointing results. Medical disk needling is a safer alternative. Needling in some instances can create over 500,000 channels within 5-10 minutes, deep into the epidermis of the skin, which is the main obstruction to penetration of active ingredients. Thus, the active ingredients in the skincare products can reach into the depths of the skin more effectively than by simply applying the products topically. Furthermore, as the active ingredients are delivered in a partially or completely controlled micro-environment, the user can modify the local micro-environment through the introduction or removal of gases in the chamber during delivery of the active ingredients. For example, the user could remove air from the chamber environment by pulling a vacuum and/or by injecting a controlled gas (e.g., an inert gas) into the chamber. Control of the micro-environment would be particularly useful when the active agent is particularly susceptible to, e.g., oxygen, temperature, light, heat, humidity, or environmental conditions that would decrease the effectiveness of the one or more active ingredients, at the skin. Disk needling creates minimal dermal damage without the removal of the healthy epidermis, which happens with other resurfacing techniques.

Figure 1:
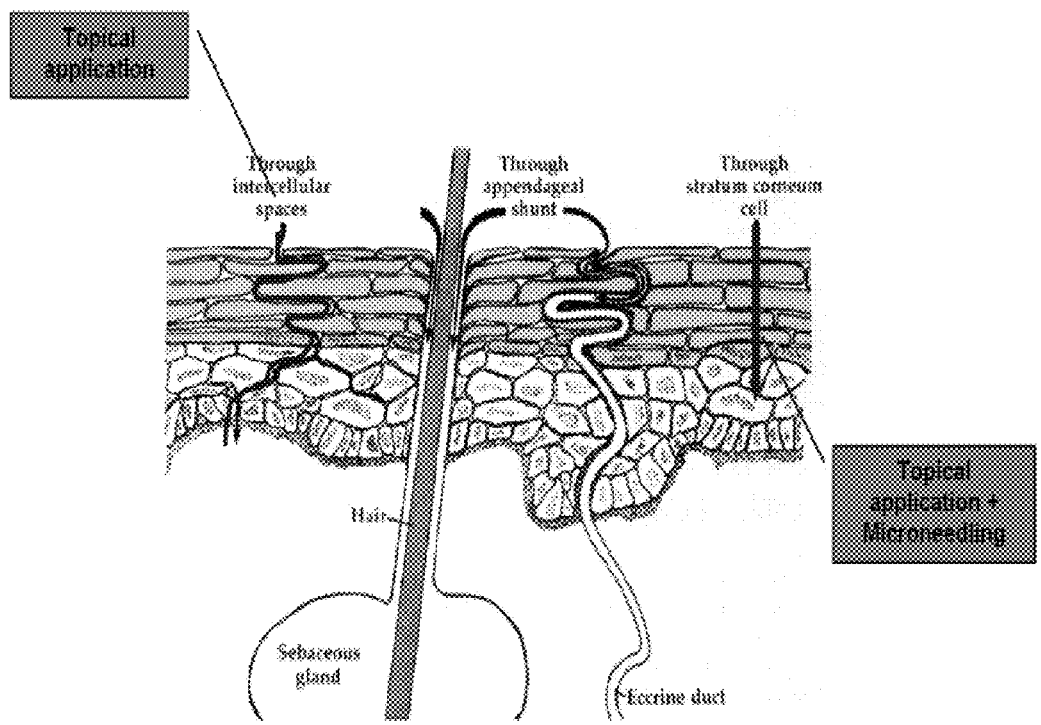
FIG. 1 is a depiction of a cross-sectional view of the skin comparing a topical application versus a combination of topical application and microneedling.

Generally speaking, the possibility of active ingredients to penetrate the epidermal barrier (stratum corneum) is approximately 0.3% per use, and due to the characteristics of cells such as keratinization, even this amount of active ingredient penetration cannot be expected all the time. The MNR infusion system of the present invention addresses this issue by using micro-needle rollers to greatly increase the effective penetration rate of the dermis and epidermis by forging a new transcellular route (FIG. 1) to construct a new transdermal delivery system. The MNR infusion system described herein makes an active ingredient or a skin-care product absorption route in the epidermis by the penetration of the needles into the stratum corneum.

Figure 2:
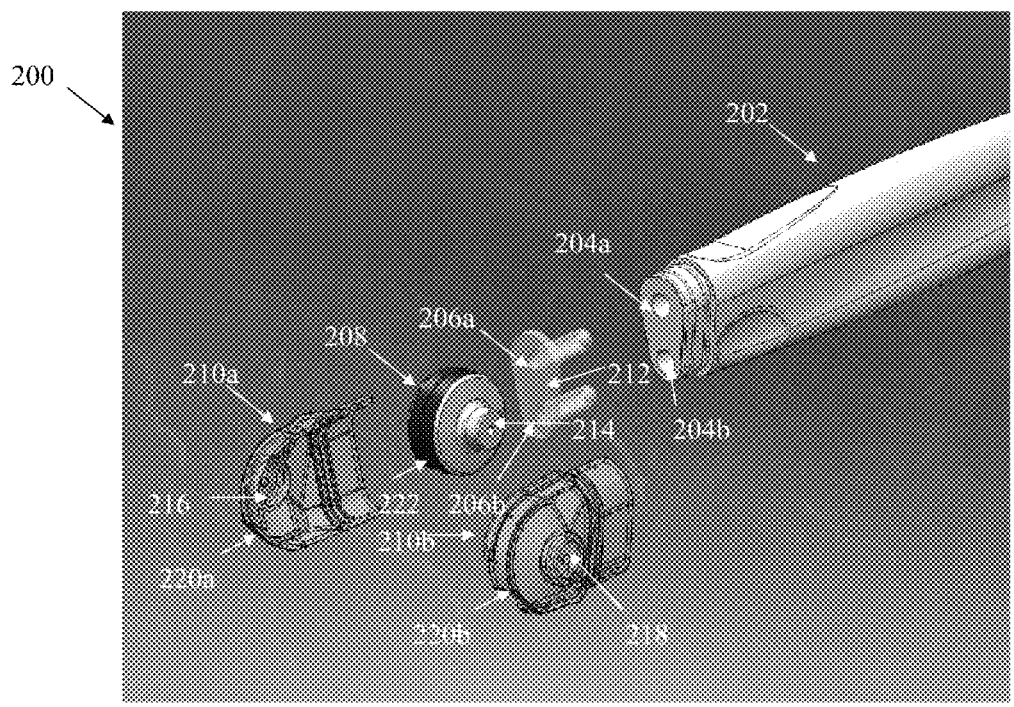
FIG. 2 is a schematic of a dual model needle-roller prototype according to an embodiment of the present invention.

The dual model needle-roller prototype 200 of the present is shown in FIG. 2. The prototype 200 has a new controller (not shown), a hand piece 202, a vacuum line (not shown), cartridge (contained in the hand piece 202) and needle roller tip cap system (assembled by joining 210a and 210b) for deeper administration of topicals than conventional infusion systems. The advantages to the market will be more effective infusion of topicals with minimal damage to the upper epidermis. The limit of penetration is to be 0.25 mm, a widely accepted penetration level (DE junction) to accomplish collagen remodeling. Current literature regarding needling without simultaneous vacuum and fluid administration, suggests that micro-channel pathways are mechanically opened up for 20 minutes to 2 hours. This is important for marketing a professional treatment.

The hand piece 202 has an enclosed cartridge comprising the active agent, the topical or the skin-care product), a reservoir for collecting any excess liquid, and a vacuum line. The opening of the cartridge 204a and the reservoir 204b in connection with the roller assembly through through tubes 206a and 206b, which are attached to a plate 212, to prevent any leakage of the ingredients in the cartridge and the reservoir during replacement of the needle or when the device is not being used. 204a and 204b respectively. The roller assembly 208 comprises a surface 222 with 0.25 mm microneedles. The tip cap for enclosing the roller assembly is made by fusing 210a and 210b. Roller assembly 208 comprises of two pins (only one of which 214 is shown) which fit into the grooves 216 and 218 in parts 210a and 210b, respectively. Tip caps 210a and 210b comprise openings 220a and 220b that enable contact of the skin with the device for the micro-needle treatment.

Disposables include the needle roller tip 210, cartridges approximately 10 ml in volume and enough to complete an entire face treatment. The disposable kit to include one roller tip 210 along with 6 cartridges. The kit is to be dedicated to one patient and discarded after the treatment series. Customers are to purchase the entire kit before treatment series begins.

The micro-needle roller used the disk needle therapy (DTS) rollers from Hansderma, Korea. The 0.25 mm roller is capable of being incorporated in a tip design compatible with the current dual mode hand piece (See FIG. 2). This allows the determination of optimal vacuum levels for fluid flow rate and for pulling skin in against the slightly recessed needle roller.

Figure 3:
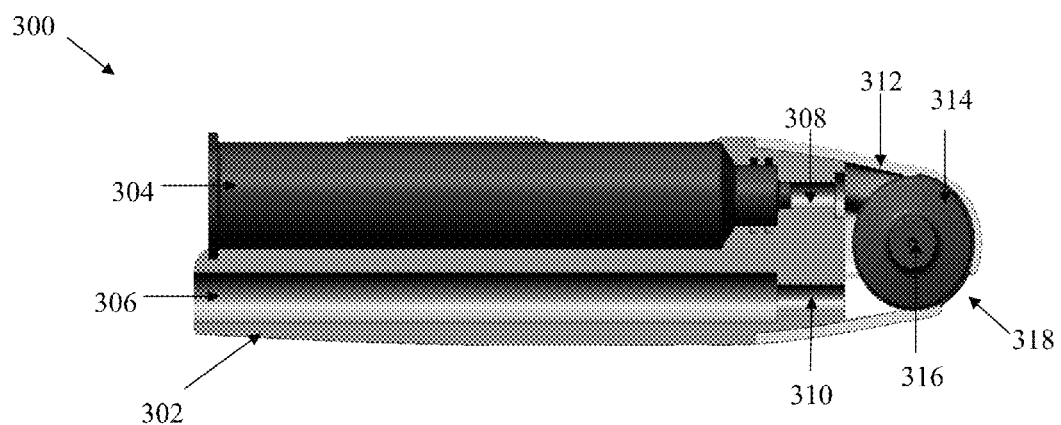
FIG. 3 is a sectional representation of the assembled micro-needle roller infusion system of the present invention, showing the internal components.

FIG. 3 is a sectional view of the MNR infusion device 300 of the present invention, showing the positions of the internal components. The infusion device 300 comprises a hand piece 302, that encloses a disposal supply cartridge 304 (10 ml) containing the active ingredient, the skin-are product or other topical applications and a reservoir 306 for collecting any excess liquid. The cartridge 304 and the reservoir 306 are in connection with the micro-needle roller 314 through two small tubes 308 and 310 respectively. The diameter of the orifice or the tube 308 allows the control of the flow rate based upon the viscosity of the fluid in the cartridge 304. Water-like fluids typically use diameters in the range of 0.005 to 0.01 inches. More viscous fluids will require larger orifice diameters. The cartridge 304 can be designed to minimize the presence of air in the fluid chamber to prevent flow problems and undesirable air pockets by the use of a plunger or a similar device, in some cases however presence of air in the cartridge 304 may be desirable in order to make a fluid and air mixture flow.

The micro-needle 314 is enclosed in a tip cap 312 that has an opening 318 for allowing contact of the micro-needle 314 with the subject's skin. The cap 312 fits the micro-needle 314 through two grooves in the body of the cap 312 (not shown here). The two projections (only one of which 316 is shown herein) on the micro-needle 314 fit into the two grooves of the body cap 312.

The MNR infusion system described herein can be used for: (i) skin rejuvenation using a peptide infusion solution from OBI Baton Rouge, La., (ii) pigment resolution using a lightening infusion solution (New Melafade and Wakamine solution) from Cosmetic Laboratories, (iii) to test effect on sun damage on face using an Epionce botanical solution, and (iv) for Botox-Like Wrinkle Redux from OBI Baton Rouge, La. using the current peptide with Agirelene component added.

Figure 4:
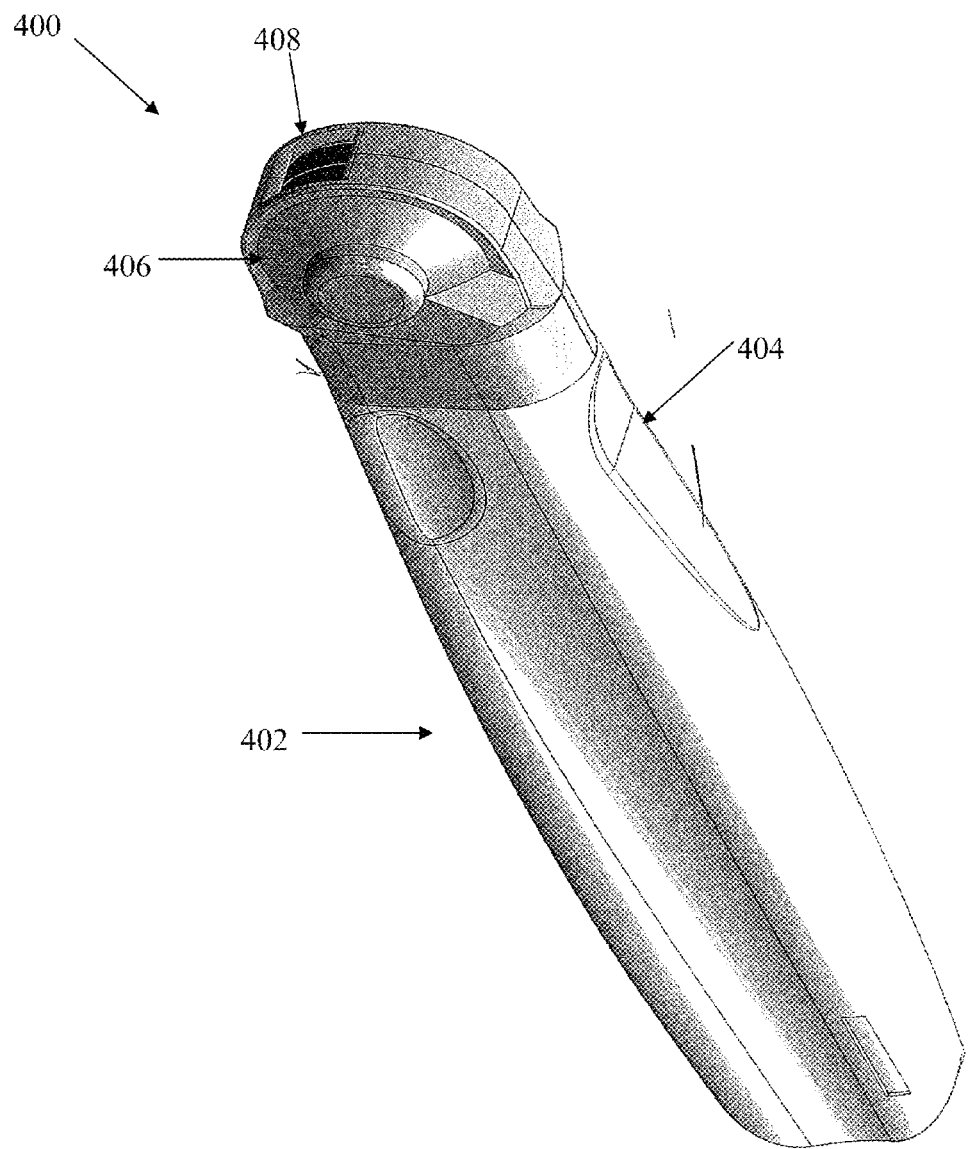
FIG. 4 shows the micro-needle roller (MNR) infusion system of the present invention.

FIG. 4 shows the fully assembled MNR infusion system 400 of the present invention. The infusion system 400 comprises a hollow hand piece 402 enclosing a vacuum line, a disposable cartridge containing the active agent, the skin-care product or the topical formulation to be infused, and a reservoir for excess fluid collection. The housing 402 also contains a switch or buttons 404 for powering on the device, turning on the vacuum, moving the roller assembly, etc. The tip-cap portion 406 is removably attached to the hand piece 402 and encloses the MNR assembly. The micro-needles penetrate the skin as skin as it rolls along with the outer housing of the tip cap 406 through the opening 408.

In the MNR infusion system described hereinabove the treatment fluid is laid onto the wheel while it rolls and the applied vacuum delivers the fluid and ensures that the skin is being pulled against the needle wheel surface. This is very important to ensure that penetration of the needles is complete into the skin. Simultaneously the fluid is flowing to the wheel and to skin as it rolls along with the outer housing of the tip cap assembly being occluded to the skin surface. Vacuum is doing two things pulling fluid to the wheel and skin and pulling the skin against the wheel in a controlled fashion. The penetration of roller needles depends most upon needle count and pressure applied by the user. The roller may also remain stationary and vacuum and/or pressure used together or alternating to ensure penetration of needles and fluid flow.

The present invention can also be modified to include the option of delivering the fluid along the needle via channels that supply fluid directly along or through the needle if it is hollow. The needle wheel center would be the source of the fluid supplied via a cartridge or would be a cartridge in itself (barrel of fluid with needles radiating from the barrel surface and channels at the base of each need to allow the vacuum to pull it out to the treated surface. Pressure could also be used ultimately to help along with vacuum assisted delivery.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 7,658,728: Microneedle array, patch, and applicator for transdermal drug delivery.
U.S. Patent Application No. 20080140049: Microneedle device for transdermal transport of fluid.
U.S. Patent Application No. 20100042050: Microneedle transdermal delivery device.
WIPO Patent Application WO/2004/082469: Skin treatment system and method of use.

What is claimed is:

1. A device for a transdermal delivery of one or more active agents, skin-care products, topical formulations or combinations thereof to a subject comprising:
   a housing comprising a cavity, wherein the cavity is adapted to receive one or more gas lines, vacuum lines or both, one or more removable reservoirs, cartridges or compartments, and one or more active agents, skin-care products, topical formulations or combinations thereof are contained in the cavity or in the removable reservoirs, cartridges or compartments; and
   a tip cap assembly removably attached to the housing assembly, wherein the tip cap assembly encloses a skin penetrating device in fluid connection with the cavity in the housing, wherein the skin penetrating device comprises a micro-needle roller comprising one or more solid micro-needles attached to and supported by a roller surface, wherein a movement of the roller over the skin of the subject causes a rotation of the roller and brings the solid micro-needles into contact with the skin of the subject through an opening in the tip cap assembly resulting in a penetration of the skin and the transdermal delivery of the one or more active agents, the skin-care products, the topical formulations or combinations thereof present on the roller, wherein the one or more active agents the skin-care products, the topical formulations or combinations thereof is drawn from the cavity, one or more removable reservoirs, cartridges or compartments by a vacuum pulled through the vacuum line.

2. The device of claim 1, wherein the housing assembly further comprises a switch, a button or combinations or modifications thereof for powering the device, turning on the vacuum, or moving the roller assembly.

3. The device of claim 1, wherein a flow of the active agent to the roller surface is controlled by the vacuum.

4. The device of claim 1, wherein a pulling of the skin of the subject to the roller surface for penetration is controlled by the vacuum.

5. The device of claim 1, wherein the solid micro-needles have lengths of 0.2 mm, 0.25 mm, 0.5 mm, 1.0 mm, and 1.5 mm.

6. The device of claim 5, wherein a length of the solid micro-needle is 0.25 mm.

7. The device of claim 1, wherein the housing comprises a material selected from the group consisting of a polymer, a metal, a mineral, a ceramic, and a glass.

8. The device of claim 1, wherein the active agent comprises a formulation selected from the group consisting of a solution, a suspension, an emulsion, a lotion, a hydrogel, a semi-solid formulation, a cream, and an emollient.

9. The device of claim 1, wherein the active agent comprises a therapeutic or a prophylactic drug, wherein the drug is selected from the group consisting of analgesic agent, an anti-inflammatory agent, an antiallergic agent, a steroid, a local anesthetic, a muscle relaxant, an anti-itch agent, an anti-bacterial agent, an anti-fungal agent, and combinations and modifications thereof.

10. A method for transdermal delivery of one or more one or more active agents, skin-care products, topical formulations or combinations thereof to a subject comprising the steps of:
   identifying a subject in need of the transdermal delivery;
   providing a transdermal delivery device comprising:
   a housing assembly comprising a cavity, wherein the cavity encloses a vacuum line, a vacuum chamber or any vacuum generating device, and one or more removable reservoirs, cartridges or compartments, wherein the one or more active agents, the skin-care products, the topical formulations, or combinations thereof is contained in the one or more removable reservoirs, cartridges or compartments; and
   a tip cap assembly removably attached to the housing assembly, wherein the tip cap assembly encloses a skin penetrating device in fluid connection with the cavity in the housing, wherein the skin penetrating device comprises a micro-needle roller comprising one or more solid micro-needles attached to and supported by a roller surface;

depressing a switch or a button on the housing assembly to power-on the device and turn on a vacuum to draw the one or more active agents, skin-care products, topical formulations or combinations thereof from the one or more removable reservoirs, cartridges or compartments by the vacuum pulled through the vacuum line;

moving the roller over the skin of the subject repeatedly thereby causing a rotation of the roller; and contacting the solid micro-needles with the skin of the subject through an opening in the tip cap assembly resulting in a penetration of the skin and the transdermal delivery of the one or more active agents, the skin-care products, the topical formulations or combinations thereof present on the roller through an opening in the tip cap assembly.

11. The method of claim 10, wherein a flow of the active agent, the skin-care product or the topical formulation to the roller surface is controlled by the vacuum.

12. The method of claim 10, wherein a pulling of the skin of the subject to the roller surface for penetration is controlled by the vacuum.

13. The method of claim 10, wherein a length of the solid micro-needle is 0.25 mm.

14. The method of claim 10, wherein the housing comprises a material selected from the group consisting of a polymer, a metal, a mineral, a ceramic, and a glass.

15. The method of claim 10, wherein the active agent, the skin-care product or the topical formulation is selected from the group consisting of a solution, a suspension, an emulsion, a lotion, a hydrogel, a semi-solid formulation, a cream, and an emollient.

16. The method of claim 10, wherein the active agent comprises a therapeutic or a prophylactic drug, wherein the drug is selected from the group consisting of analgesic agent, an anti-inflammatory agent, an antiallergic agent, a steroid, a local anesthetic, a muscle relaxant, an anti-itch agent, an anti-bacterial agent, an anti-fungal agent, and combinations and modifications thereof.

17. The method of claim 10, wherein the skin-care products are selected from the group consisting of cleansers, toners, exfoliants, moisturizers, boosters, skin rejuvenating agents, anti-wrinkle agents, dry vacuum needling, and combinations or modifications thereof.

18. A method of treating a skin condition in a subject by a delivery of one or more one or more active agents, skin-care products, topical formulations or combinations thereof to a subject comprising the steps of:
   identifying a subject in need of treatment against the skin condition;
   providing a transdermal delivery device comprising:
      a housing assembly comprising a cavity, wherein the cavity encloses a vacuum line, a vacuum chamber or any vacuum generating device, and one or more of removable reservoirs, cartridges or compartments, wherein the one or more active agent, the skin-care products, the topical formulations or combinations thereof is contained in the one or more removable reservoirs, cartridges or compartments; and
      a tip cap assembly removably attached to the housing assembly, wherein the tip cap assembly encloses a skin penetrating device in fluid connection with the cavity in the housing, wherein the skin penetrating device comprises a micro-needle roller comprising one or more solid micro-needles attached to and supported by a roller surface, depressing a switch or a button on the housing assembly to power-on the device and turn on a vacuum to draw the active agent, skin-care products, topical formulations or combinations thereof from the one or more removable reservoirs, cartridges or compartments by the vacuum pulled through the vacuum line;

moving the roller over the skin of the subject repeatedly thereby causing a rotation of the roller; and contacting the solid micro-needles with the skin of the subject through an opening in the tip cap assembly resulting in a penetration of the skin and the transdermal delivery of the one or more active agents, the skin-care products, the topical formulations or combinations thereof present on the roller through an opening in the tip cap assembly.

19. The method of claim 18, wherein the skin conditions are selected from the group consisting of bacterial, viral and fungal skin infections, skin rashes, itching, redness, swelling, burning, itching, allergies, dermatitis, hives, acne, psoriasis, eczema, wrinkles, dryness, rosacea, shingles, sunburn, skin cancers, flakes, scars, striae, and combinations and modifications thereof.

20. The method of claim 18, wherein a flow of the active agent, the skin-care product or the topical formulation to the roller surface is controlled by the vacuum.

21. The method of claim 18, wherein a pulling of the skin of the subject to the roller surface for penetration is controlled by the vacuum.

22. The method of claim 18, wherein a length of the solid micro-needle is 0.25 mm.

23. The method of claim 18, wherein the active agent comprises a therapeutic or a prophylactic drug, wherein the drug is selected from the group consisting of analgesic agent, an anti-inflammatory agent, an antiallergic agent, a steroid, a local anesthetic, a muscle relaxant, an anti-itch agent, an anti-bacterial agent, an anti-fungal agent, and combinations and modifications thereof.

24. The method of claim 18, wherein the skin-care products are selected from the group consisting of cleansers, toners, exfoliants, moisturizers, boosters, skin rejuvenating agents, anti-wrinkle agents, dry vacuum needling, and combinations or modifications thereof.

25. A device for a transdermal delivery of one or more active agents, skin-care products, topical formulations or combinations thereof to a subject comprising:
   a housing assembly comprising a cavity, wherein the cavity encloses a vacuum line, a vacuum chamber or any vacuum generating device, and one or more of removable reservoirs, cartridges or compartments, wherein the one or more active agents, the skin-care products, the topical formulations or combinations thereof is contained in the one or more removable reservoirs, cartridges or compartments; and
   a tip cap assembly removably attached to the housing assembly, wherein the tip cap assembly encloses a skin penetrating device in fluid connection with the cavity in the housing, wherein the skin penetrating device comprises a micro-needle roller, wherein one or more solid micro-needles attached to and supported by a roller surface, wherein a movement of the roller over the skin of the subject causes a rotation of the roller and brings the solid micro-needles into contact with the skin through an opening in the tip cap assembly resulting in a penetration of the skin and the transdermal delivery of the one or more active agents, the skin-care products, the topical formulations or combinations thereof along the solid micro-needles.

26. The device of claim 25, wherein a flow of the active agent, the skin-care product or the topical formulation to the solid micro-needles is controlled by the vacuum.

27. The device of claim 25, wherein a pulling of the skin of the subject to the roller surface for penetration is controlled by the vacuum.

28. A device for a transdermal delivery of one or more active agents, skin-care products, topical formulations or combinations thereof to a subject comprising:

a housing assembly comprising a cavity, wherein the cavity encloses a vacuum line, a vacuum chamber or any vacuum generating device, and one or more of removable reservoirs, cartridges or compartments, wherein the one or more active agents, the skin-care products, topical formulations or combinations thereof is contained in the one or more removable reservoirs, cartridges or compartments; and a tip cap assembly removably attached to the housing assembly, wherein the tip cap assembly encloses a skin penetrating device in fluid connection with the cavity in the housing, wherein the skin penetrating device comprises a micro-needle roller, wherein one or more solid micro-needles are attached to and supported by a roller surface, wherein a movement of the roller over the skin of the subject causes a rotation of the roller and brings the solid micro-needles into contact with the skin through an opening in the tip cap assembly resulting in a penetration of the skin and the transdermal delivery of the one or more active agents, the skin-care products, the topical formulations or combinations thereof along the solid micro-needles, wherein the one or more active agents, the skin-care products, the topical formulations or combinations thereof is drawn from the one or more removable reservoirs, cartridges or compartments by a vacuum pulled through the vacuum line.

29. The device of claim 28, wherein a flow of the active agent, the skin-care product or the topical formulation to the solid micro-needles is controlled by the vacuum.

30. The device of claim 28, wherein a pulling of the skin of the subject to the roller surface for penetration is controlled by the vacuum.

31. The device of claim 28, wherein the active agent comprises a formulation selected from the group consisting of a solution, a suspension, an emulsion, a lotion, a hydrogel, a semi-solid formulation, a cream, and an emollient.

32. The device of claim 28, wherein the active agent comprises a therapeutic or a prophylactic drug, wherein the drug is selected from the group consisting of analgesic agent, an anti-inflammatory agent, an antiallergic agent, a steroid, a local anesthetic, a muscle relaxant, an anti-itch agent, an anti-bacterial agent, an anti-fungal agent, and combinations and modifications thereof.

33. The device of claim 28, wherein the solid micro-needles have lengths of 0.2 mm, 0.25 mm, 0.5 mm, 1.0 mm, and 1.5 mm.

34. The device of claim 28, wherein the skin-care products are selected from the group consisting of cleansers, toners, exfoliants, moisturizers, boosters, skin rejuvenating agents, anti-wrinkle agents, dry vacuum needling, and combinations or modifications thereof.

* * * * *